United States Patent [19]
Mathus et al.

[11] Patent Number: 5,856,176
[45] Date of Patent: Jan. 5, 1999

[54] CULTURE DISH

[75] Inventors: Gregory Mathus, Concord; Anthony M. Labriola, Woburn, both of Mass.

[73] Assignee: Corning Incorporated, Corning, N.Y.

[21] Appl. No.: 625,728

[22] Filed: Mar. 29, 1996

[51] Int. Cl.$^6$ ............................................. C12M 3/00
[52] U.S. Cl. ........................... 435/288.3; 435/305.3; 220/755; 220/768; 220/769; 220/771; 220/772
[58] Field of Search ..................... 435/288.3, 305.1, 435/305.3, 305.4; 422/102; 220/755, 768, 769, 771, 772

[56] References Cited

U.S. PATENT DOCUMENTS

| | | |
|---|---|---|
| 2,677,646 | 5/1954 | Lovell et al. . |
| 2,677,647 | 10/1954 | Lovell ................................. 435/305.4 |
| 3,630,849 | 12/1971 | Land et al. . |
| 3,649,463 | 3/1972 | Buterbaugh . |
| 3,870,602 | 3/1975 | Froman et al. ......................... 195/139 |
| 3,886,047 | 5/1975 | Billups, Jr. . |
| 4,012,288 | 3/1977 | Lyman et al. ........................... 195/139 |
| 4,160,700 | 7/1979 | Boomus et al. ......................... 435/298 |
| 4,321,330 | 3/1982 | Baker et al. ............................ 435/301 |
| 4,435,508 | 3/1984 | Gabridge ................................ 435/284 |
| 4,634,676 | 1/1987 | Sapatino ................................ 435/294 |
| 4,988,302 | 1/1991 | Smith et al. ......................... 435/305.4 |
| 5,021,351 | 6/1991 | Ervin .................................... 435/297 |
| 5,310,676 | 5/1994 | Johansson et al. ..................... 435/285 |
| 5,520,302 | 5/1996 | Anderson et al. ...................... 220/335 |

FOREIGN PATENT DOCUMENTS

| | | |
|---|---|---|
| 1206119 | 12/1965 | Germany . |
| 41 33 798 A1 | 4/1992 | Germany . |
| 43 00 231 C1 | 12/1993 | Germany . |

*Primary Examiner*—David A. Redding
*Attorney, Agent, or Firm*—Wolf, Greenfield & Sacks, P.C.

[57] ABSTRACT

A culture dish for growing cultures such as tissue cells, bacteria and the like. The culture dish includes a handle extending therefrom that can be easily grasped by a user when lifting or handling the culture dish. The culture dish can also include a lid that can be placed on a base of the dish to prevent contamination of the cultures and to control evaporation of liquid from the dish. The handle can extend from the base, the lid or both. If the handles are provided on both the base and the lid, they can be configured differently so that a user can readily distinguish between them.

22 Claims, 5 Drawing Sheets

CULTURE DISH

BACKGROUND OF THE INVENTION

1. Field of the Invention

The present invention relates to a culture dish that is stackable and includes features that enable a user to easily handle the dish.

2. Description of the Related Art

Culture dishes are known and widely used in laboratory environments for growing cell cultures, bacteria, viruses and the like. In the cell growth application, cell cultures are grown from tissue cell samples that are placed in the dish and covered with a liquid medium that promotes cell growth when the dish is placed in a controlled environment such as an incubator. For this application, the culture dish is typically sterilized and treated to promote the binding of cells to the dish surface. The grown cells can be removed from the dish to facilitate examination, or the user can examine the cells while in the dish, using an instrument such as a microscope. In another conventional application, tissue cells are grown in a semisolid (rather than liquid) medium that does not bind to the dish. Thus, the medium can be readily removed to recover the cells by simply turning over the dish.

A further conventional application for culture dishes is in the molecular biology field in which cultures such as bacteria and the like can be grown in or on an agar-based medium within the dish. Plaque lifts of the cultures grown on the medium are taken for examination by laying a membrane over the medium and on the cultures, and then lifting the membrane from the medium.

To control evaporation of the medium and prevent contamination of the cultures, culture dishes generally include a base for receiving the cultures and a lid that can be placed on the base to cover it. The lid may be transparent to provide a viewing panel enabling visual examination of the cultures while the lid is in place. Culture dishes are also generally designed so that one dish can be stacked on top of another to make efficient use of laboratory resources (e.g., an incubator) shared by multiple dishes, and to facilitate transport of a number of culture dishes from one location to another.

A disadvantage of known culture dishes is that they are difficult to handle. For example, when the culture dish includes a lid, the user may have difficulty in sliding his fingers under the base to lift the dish, because the lid is wider and overlaps the base. Thus, the user may not be able to feel whether he is actually grasping the base, or just the lid. Alternatively, if a culture dish is handled with its lid removed, the cultures can become contaminated by the user's thumbs extending over the edge of the dish when grasped from the sides.

Another difficulty in handling conventional culture dishes involves lifting the dish from a surface, which requires a user to first lift an edge of the dish so that he can slide his fingers below the base. This can cause liquid growth medium to spill from the dish, even when covered with a lid. This difficulty can be compounded when a user attempts to lift a stack of multiple culture dishes.

Accordingly, it is an object of the present invention to provide an improved culture dish.

SUMMARY OF THE INVENTION

In one illustrative embodiment of the invention, an apparatus is provided comprising a culture dish and at least one handle extending from the culture dish.

In another illustrative embodiment of the invention, an apparatus is provided comprising a culture dish including a base having a bottom wall, a rim and a sidewall extending upwardly from the bottom wall to the rim. The sidewall includes a lower sidewall and an upper sidewall, the lower sidewall being disposed between the bottom wall and the upper sidewall, the upper sidewall being disposed between the lower sidewall and the rim. The lower sidewall is angled at a first angle relative to a vertical plane passing through the bottom wall, and the upper sidewall is angled at a second angle relative to the vertical plane, wherein the first angle is different than the second angle.

In yet another illustrative embodiment of the invention, an apparatus is provided comprising a culture dish and means, disposed on the culture dish, for facilitating handling of the culture dish.

BRIEF DESCRIPTION OF THE DRAWINGS

It should be understood that the drawings are provided for the purpose of illustration only and are not intended to define the limits of the invention. The foregoing and other objects and advantages of the present invention will become apparent with reference to the following detailed description when taken in conjunction with the following drawings, in which.

DETAILED DESCRIPTION OF THE INVENTION

Figure 1:
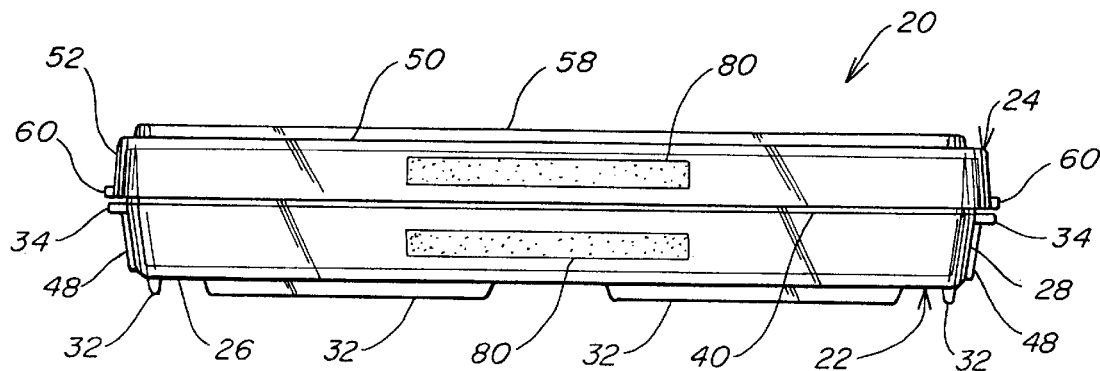
FIG. 1 is a front elevational view of a culture dish of the present invention.

The present invention is directed to a culture dish that can be used for growing cultures such as tissue cells, bacteria, viruses and the like. An illustrative embodiment of a culture dish 20 according to the present invention is shown in FIGS. 1–6B, and includes a base 22 and a lid 24. The cultures are grown in the base 22, with the lid 24 being placed over the base 22 primarily to prevent contamination of the cultures and to control evaporation of a liquid growth medium. The lid 24 can also function as a platform upon which other culture dishes 20 can be stacked to facilitate the simultaneous handling of a plurality of culture dishes, and to make more efficient use of laboratory resources, such as incubators, shared by multiple dishes. As illustrated, the culture dish 20 has a generally square shape with rounded corners which is conventional so that the dish is compatible with automated process equipment that has been developed for use with culture dishes shaped in this manner. However, it should be understood that the invention is not limited in this respect, and that a number of other dish shapes are possible. In one embodiment as shown in FIG. 2, the dish has an overall width $W_1$ (excluding the handles discussed below) of approximately 9.43 inches and an overall height $H_1$ of approximately 1.01 inches. However, the present invention is not limited to these specific dimensions.

The base 22 and lid 24 can each be of a unitary molded construction formed from a plastic material. In one embodiment of the invention, the base 22 and lid 24 are molded from a transparent polymer, such as polystyrene, to facilitate the visual inspection of the cultures in the dish 20. However, it should be understood that other materials can also be used.

The base 22 includes a substantially planar bottom wall 26 and a continuous sidewall 28 extending upwardly from the bottom wall 26 along its entire periphery to form an upwardly facing cavity 30 (FIG. 5A) within which cultures can be grown. As described in more detail below, the sidewall 28 is formed with multiple angles to facilitate the molding process, and to reduce the external footprint of the dish.

Figure 4:
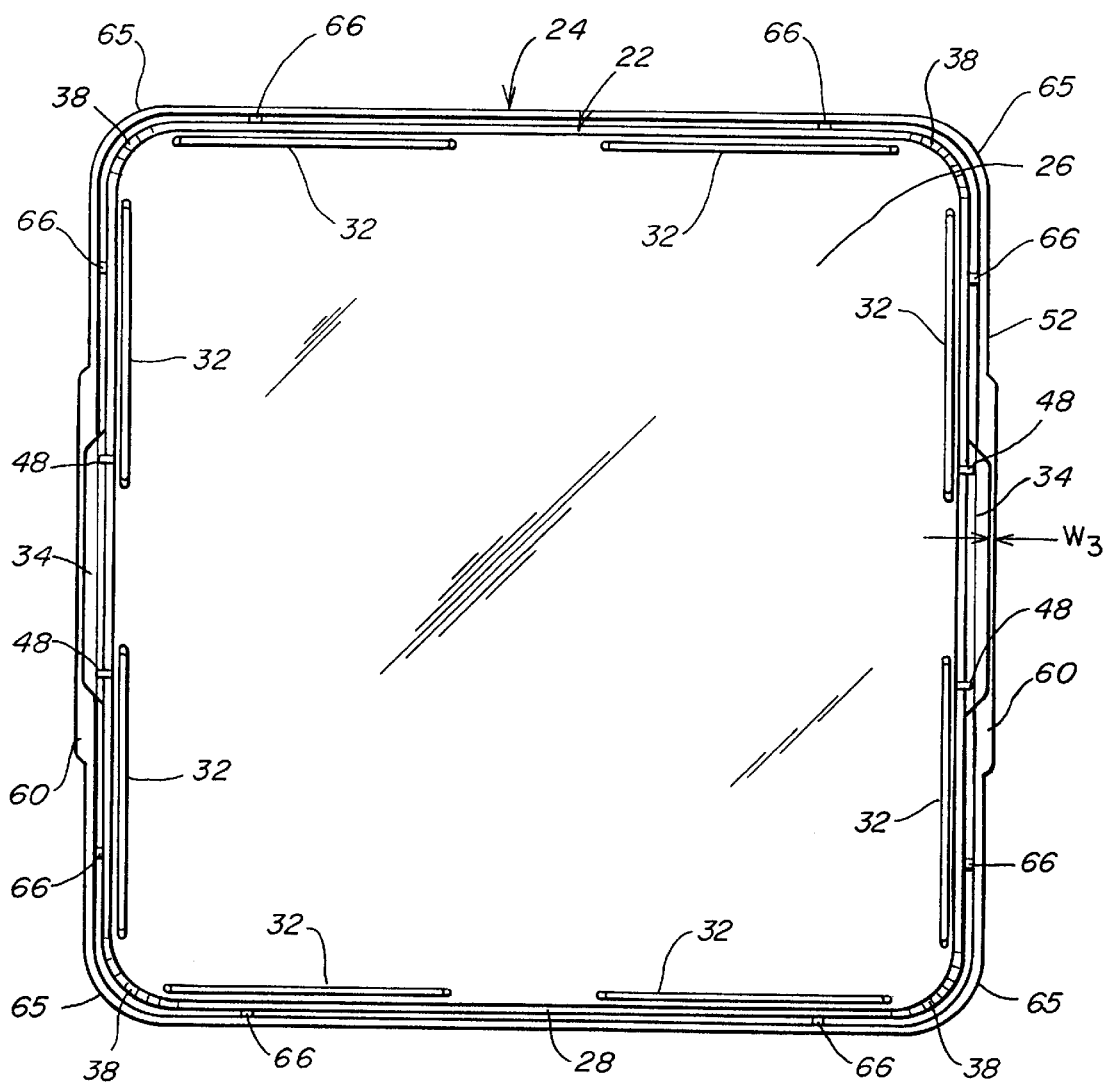
FIG. 4 is a bottom plan view of the dish of FIG. 1.

The base 22 includes a plurality of beads 32 extending downwardly from the periphery of the underside of the bottom wall 26. As best illustrated in FIG. 4, two elongated beads 32 extend along each edge of the bottom wall 26. The beads 32 raise the bottom wall 26 above a supporting surface so that the bottom wall will not contact and be scratched by the surface. Furthermore, the beads 32 are configured to interlock with the lid 24 of an identical culture dish in a stacked configuration to prevent the dishes from sliding relative to each other when the stack is lifted or moved from one location to another. In the embodiment of the invention shown in the figures, the beads 32 are spaced from each other along the bottom wall periphery so that air can circulate between adjacent stacked culture dishes 20, thereby ensuring uniform temperature distribution across the bottom of each dish when a stack is placed in a controlled growth environment such as an incubator. The circulation of air can also limit the development of condensation between adjacent dishes, and prevent a vacuum or fluid lock between the dish and a surface on which it is disposed, such as another dish on which it is stacked or a laboratory bench. For example, the spaces prevent a layer of fluid from building up between the base and the surface on which it is disposed, which could hydraulically lock the two together, making it difficult to separate them.

As shown in FIGS. 1–4, the base 22 of the culture dish of the present invention includes a pair of base handles 34 that can be grasped by a user to facilitate handling of the dish. The base handles 34 are relatively thin members that protrude outwardly from opposing portions of the base sidewall 28 intermediate the bottom wall 26 and an upper rim 36 of the base sidewall. In the embodiment shown, the base handles 34 are centrally located along the sidewall between the corners 38 of the base, protrude from the sidewall in a generally horizontal plane and extend lengthwise along the opposing portions of the sidewall 28. However, it should be understood that other configurations are possible.

The culture dish of the present invention can be used in some applications wherein it may share laboratory resources (e.g., incubator space) with a number of other dishes. Thus, it is desirable to minimize the distance by which the handles protrude from the sidewall, to minimize the external footprint of the dish. Therefore, the handles preferably extend beyond the sidewall just enough for them to be easily grasped. In one embodiment of the invention, the base handles 34 protrude from the sidewall 28 ($W_2$ in FIG. 5A) by approximately 0.17 inches, although this dimension can obviously be varied.

Figure 5A:
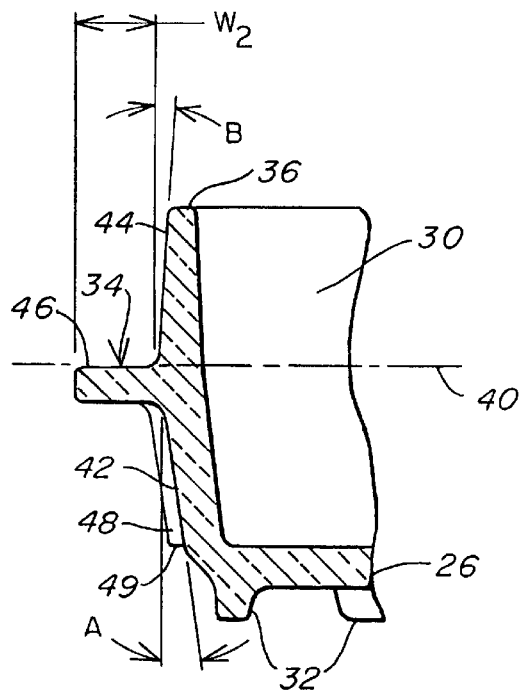
FIG. 5A is a partial cross-sectional view of the base of the culture dish of FIGS. 1–4 taken along section line 5—5 in FIG. 3.
Figure 6A:
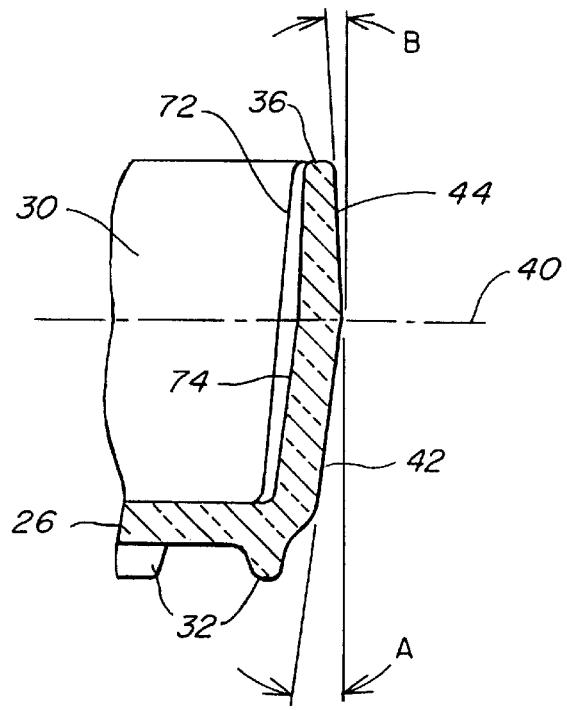
FIG. 6A is a partial cross-sectional view of the base of the culture dish of FIGS. 1–4 taken along section line 6—6 in FIG. 3.

As best shown in FIGS. 5A and 6A, the base sidewall 28 can be formed with multiple draft angles A and B that reverse direction relative to each other along the height of the sidewall to facilitate molding of the base 22, and to reduce the external footprint of the dish. The sidewall 28 has a parting line 40 that defines a lower sidewall portion 42 and an upper sidewall portion 44. The lower sidewall 42 is angled inwardly from the parting line 40 as it extends downwardly toward the bottom wall 26. Similarly, the upper sidewall 44 is angled inwardly from the parting line 40 as it extends upwardly toward the sidewall upper rim 36. In one embodiment of the invention, each base handle 34 is disposed on the lower sidewall 42 so that the upper surface 46 of the handle protrudes from the sidewall 28 at the parting line 40. This simplifies the molding process by allowing the use of a relatively simple and inexpensive mold. Angling the upper sidewall 44 inwardly also advantageously allows the use of a slightly smaller lid 24 to cover the base 22, as compared to a lid that would be required if the sidewall angled continuously outwardly from the bottom wall to the upper rim, thereby reducing the external footprint of the dish.

In some applications, it may be desirable to stack a plurality of culture dish bases 22, without lids, on top of each other. Accordingly, in one embodiment of the invention, the culture dish is provided with a feature that enables it to be stacked in the base of another dish with the beads 32 of the dish sitting above the bottom wall 26 of the receiving dish to enable air circulation between the stacked dishes, thereby providing uniform temperature distribution across the upper dish and preventing interference with the cultures in the lower dish. In the embodiment shown in the figures, this feature includes a pair of standoffs 48 (best shown in FIGS. 2, 5A and 5C) formed on the outer surface of the lower sidewall 42 below and adjacent each end of the handles 34. The standoffs 48 are integrally connected to the bottom of the handle and extend down the lower sidewall 42 where they terminate in a shoulder 49 that is adapted to engage the upper rim 36 of a base 22 on which the dish is stacked. It should be understood that a number of alternate configurations can also be used to achieve separation between two stacked bases, and that the particular configuration shown in the figures is provided merely for illustration.

As shown in FIGS. 1–4, the lid 24 includes a generally square planar top wall 50 and a continuous sidewall 52 extending downwardly from the periphery of the top wall. The lid sidewall 52 forms a downwardly facing cavity 54 (FIG. 5B) that is configured to receive the upper sidewall 44 of the base 22, thereby creating an essentially closed dish cavity. In one embodiment, the sidewall 52 is angled outwardly from the top wall 50 as it extends downwardly toward a lower lid rim 56 at an angle C that corresponds to the angle B of the base upper sidewall 44 to minimize to profile of the lid.

In the embodiment shown in the figures, the lid 24 includes a continuous interlocking wall 58 (FIG. 3) protruding upwardly from an upper surface of the lid and extending along its periphery. The interlocking wall 58 is configured to receive and interlock with the beads 32 of a base that is placed on the lid 24 in a stacked configuration. The height of the interlocking wall 58 ($H_3$ in FIG. 2) is preferably less than the height of the beads 32 ($H_2$ in FIG. 2), for example 0.060 and 0.075 inches, respectively, so that when two dishes are stacked together, the bottom wall 28 of the upper dish does not engage the interlocking wall of the lower dish, thereby allowing air circulation between the stacked dishes. As described above, this allows for uniform temperature distribution across the bottom of the upper dish, and avoids condensation build up and creation of a fluid or vacuum lock between the dishes. Alternatively, the height of the interlocking wall can be made equal to or greater than the height of the beads 32, and the interlocking wall can be interrupted to allow for air circulation between stacked dishes. It should also be understood that the lid 24 can alternatively include other interlocking features, such as multiple recesses disposed to receive the base beads of a dish stacked atop it.

Figure 5B:
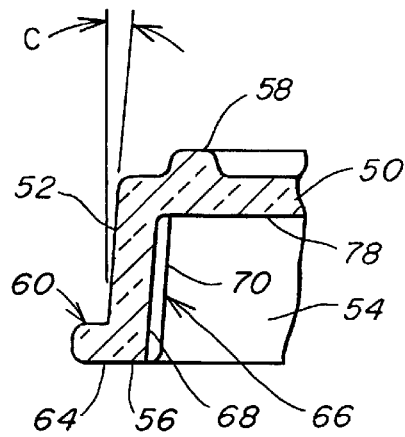
FIG. 5B is a partial cross-sectional view of the lid of the culture dish of FIGS. 1–4 taken along section line 5—5 in FIG. 3.
Figure 5C:
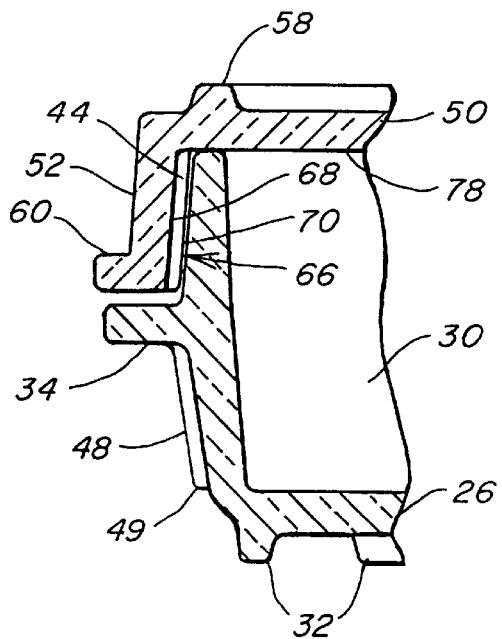
FIG. 5C is a partial cross-sectional view of the culture dish of FIGS. 1–4 taken along section line 5—5 in FIG. 3.

To facilitate the handling of the lid 24, a pair of lid handles 60 is formed on opposing portions of the lid sidewall 52 as shown in FIGS. 1–4. Similar to the base handles 34 described above, each lid handle 60 is a relatively thin member that protrudes outwardly from the sidewall 52 in a generally horizontal plane and extends lengthwise along opposing portions of the sidewall 52. In one embodiment, each lid handle 60 is disposed on the sidewall 52 so that the lower surface 64 of the handle lies in the same plane as the lid rim 56 (FIG. 5B). This simplifies the molding process by allowing the use of a relatively simple and inexpensive mold. Each handle 60 is located between the lid corners 65 so that it overlies the base handle 34 when the lid 24 is placed on the base 22. As shown in the figures, each lid handle can be centered between the lid corners.

In one embodiment of the invention, best shown in FIGS. 2 and 4, the length $L_1$ (e.g., 3.50 inches) of the lid handle 60 is longer than the length $L_2$ (e.g., 2.80 inches) of the base handle 34, so that a user can easily grasp only the lid handle 60 to remove the lid 24 from the base 22. This result can be achieved in other ways. For example, as shown in FIG. 4 ($W_3$), the lid handle 60 can protrude from the culture dish by a slightly greater amount (e.g., 0.02 inches) than the base handle 34. In the embodiment of the invention shown in the figures, both techniques are employed. It should be understood that other dimensions are possible.

For some applications of the culture dish 20, such as growing tissue cells, it is necessary that an exchange of gases occur between the base cavity 30 and the ambient atmosphere. Therefore, it is desirable that the lid 24 and the base 22 be configured so that they do not form an airtight seal that would prevent the gas exchange. In one embodiment of the invention, the lid 24 is formed so that it fits loosely on the base 22, with the top wall 50 of the lid being supported on the base rim 36 and the lid sidewall 52 being spaced from the upper sidewall 44 of the base 22. Due to slight warpage in the parts that results from the molding process, gaps exist between the lid top wall and the base rim, so that no airtight seal is formed. Therefore, gases can pass through these gaps to provide the gas exchange needed for growing tissue cells. It should be understood that the dish can include other features to enable gas exchange. For example, the lid and base can be configured so that the lid is supported above the base upper rim, or apertures can be formed in the base sidewall or the lid.

In one embodiment of the invention, a feature is provided to prevent the oversized lid from undesirably sliding relative to the base due to the free play between the lid and base sidewalls. In the embodiment shown in FIGS. 5B, 5C and 6B, the lid 24 includes a plurality of spacers 66 that reduces the amount of free play between the base 22 and the lid 24 while maintaining a spaced relation between the lid sidewall 52 and the base upper sidewall 44. As shown, the spacers 66 are inwardly projecting vertical ribs formed on the inner surface 68 of the lid sidewall 52. The spacers 66 have an angled outer edge 70 that is configured to engage the upper sidewall 44 when the lid 24 is displaced toward the base 22, thereby maintaining the lid sidewall in a relatively fixed spaced relation from the base 22. As illustrated in FIG. 4, a pair of spacers 66 is symmetrically disposed on each portion of the lid sidewall 52 between the lid corners 65. However, it should be understood that the number and location of the spacers can be varied, and that other configurations can also be used to reduce sliding of the lid relative to the base.

Figure 3:
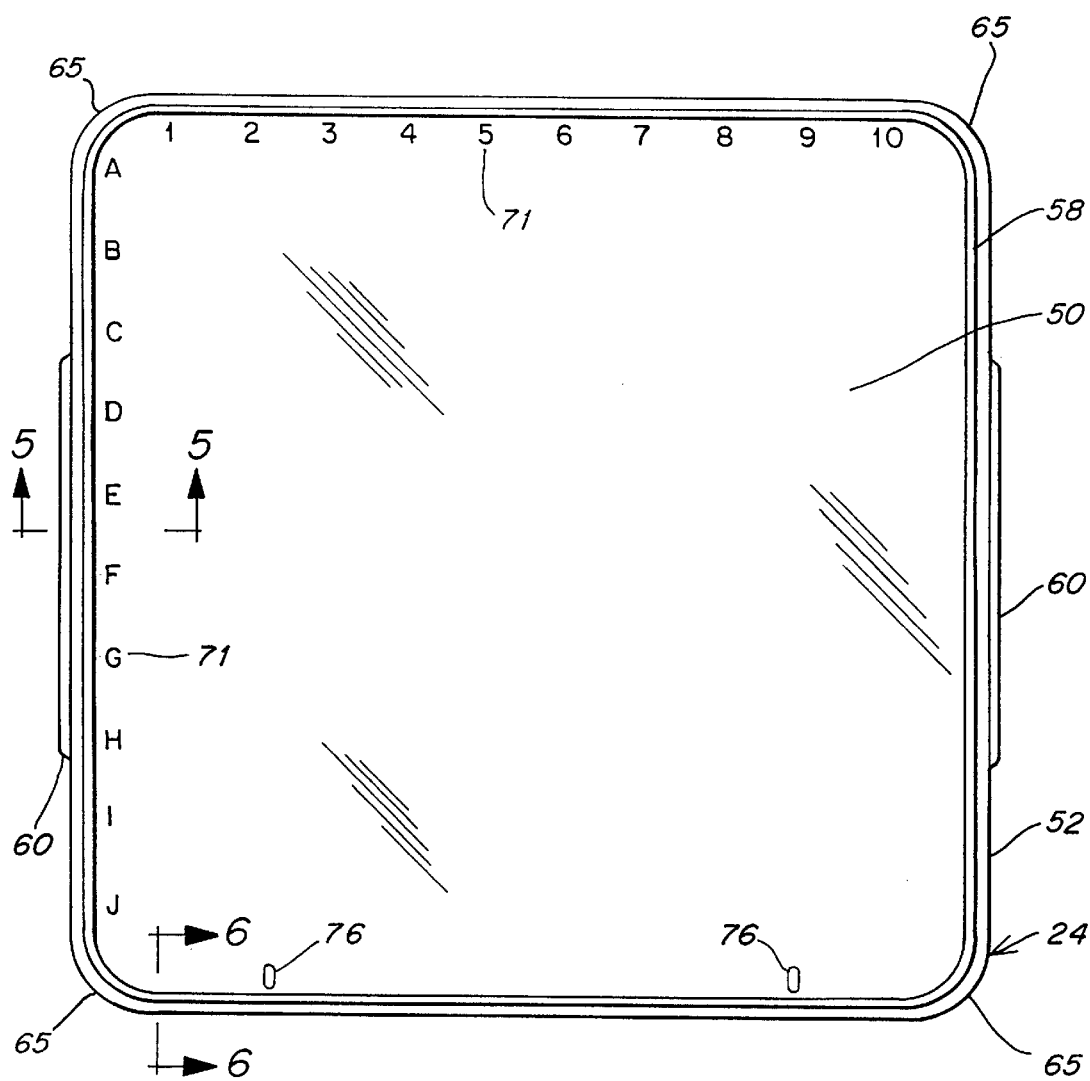
FIG. 3 is a top plan view of the dish of FIG. 1.

As shown in FIG. 3, the lid can include a plurality of characters 71 that are molded on the upper surface of the top wall 50. The characters 71 enable a user to identify the location of particular cultures being grown in the culture dish 20. One series of characters is disposed along one edge of the lid, and another is disposed along an adjacent edge. Each culture location is identified by the unique intersection between a row identified by one character and a column identified by another. Both series of characters are disposed within the perimeter of and adjacent the interlocking wall 58. In the embodiment shown in the figures, one series of characters is alphabetical and the other is numerical. However, it should be understood that other characters can be used to identify the culture locations, that the characters can be located elsewhere on the culture dish, and that they need not be molded.

Figure 6B:
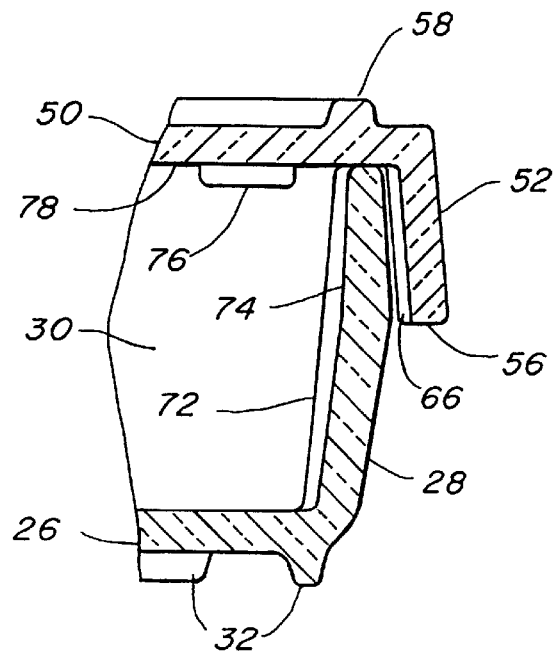
FIG. 6B is a partial cross-sectional view of the culture dish of FIGS. 1–4 taken along section line 6—6 in FIG. 3.

In one embodiment of the invention, the base and lid include orientation features that are used to orientate the lid on the base to ensure that the culture locations within the base 22 are consistently identified. This is particularly useful if the lid is removed and then replaced on the base. In one embodiment shown in FIGS. 6A and 6B, a visual indicator is provided in the form of a pair of orientation tabs 72 disposed on the inside surface 74 of one portion of the base sidewall 28. The orientation tabs 72 extend vertically between the bottom wall 26 and the upper rim 36 of the sidewall. As shown in FIGS. 3 and 6B, the lid 24 includes a pair of elongated orientation bosses 76 disposed on the inner surface 78 of the top wall 50. The bosses 76 depend downwardly from the inner surface 78 of the top wall and are disposed so they are adjacent the orientation tabs 72 when the lid 24 is placed on the base 22 in one orientation. Because the lid 24 is made of a transparent material, the orientation bosses 76 can be viewed through the top wall 50, thereby enabling a user to line up the orientation bosses 76 with the orientation tabs 72 to ensure that the lid is properly oriented on the base. It should be understood that a number of other orientation indicators can be used, including not only alternate visual indicators, but also indicators that physically limit the possible relative orientations of the base and lid to a single orientation.

Figure 2:
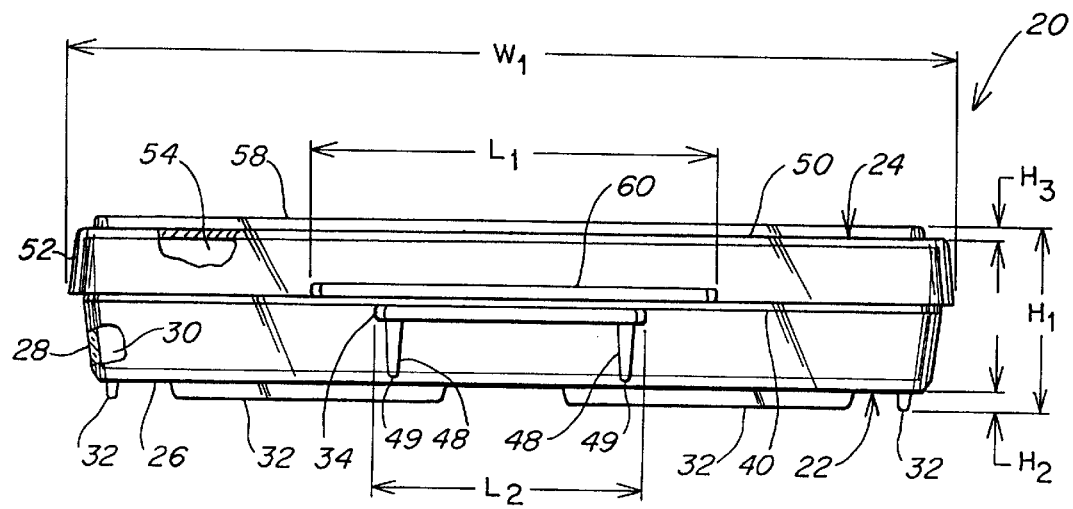
FIG. 2 is a side elevational view of the culture dish of FIG. 1.

A frosted area 80 can be provided on the outer surface of the lid sidewall 52 and/or the lower sidewall 42 of the base as shown in FIG. 1. The frosted areas 80 may be marked by the user to identify particular samples or tests with which the culture dish 20 is used.

The base and lid can each be molded using standard molding techniques (e.g., injection molding) generally known in the art. In some applications, the culture dish may be sealed in a bag to keep the dish sterile. Thus, the base and lid can be molded in a manner so that external edges are eased with a radius to reduce the potential for sharp edges slicing through sealed storage bags, which would compromise the sterility of the culture dish.

Having thus described several illustrative embodiments of the invention, various alterations, modifications and improvements will readily occur to those skilled in the art. Such alterations, modifications and improvements are intended to be within the spirit and scope of the invention. Accordingly, the foregoing description is by way of example only and is limited only as defined in the following claims and the equivalents thereto.

What is claimed is:

1. An apparatus comprising:
   a culture dish including a base having a bottom wall and a sidewall, the sidewall including a lower sidewall and an upper sidewall, the lower sidewall being disposed between the bottom wall and the upper sidewall, the lower sidewall being angled at a first angle relative to a vertical plane passing through the bottom wall, the upper sidewall being angled at a second angle relative to the vertical plane, the first angle being different than the second angle; and
   at least one handle extending from the sidewall.

2. The apparatus recited in claim 1, wherein the at least one handle is disposed on the lower sidewall.

3. An apparatus comprising:
   a culture dish including a base and a lid adapted to be disposed on the base;
   at least one first handle extending from a sidewall of the lid; and
   at least one second handle extending from a sidewall of the base, wherein the first handle overlies the second handle, the first handle having a first length that extends along the sidewall of the lid and the second handle having a second length that extends along the sidewall of the base, the first length being greater than the second length.

4. The apparatus recited in claim 3, wherein the first handle has a first outer edge disposed opposite the sidewall of the lid and the second handle has a second outer edge disposed opposite the sidewall of the base, the first and second handles being arranged so that the first outer edge protrudes beyond the second outer edge when the lid is disposed on the base.

5. The apparatus recited in claim 3, wherein each of the base and the lid includes at least two corners, the first handle being centered between the at least two corners of the lid and the second handle being centered between the at least two corners of the base.

6. The apparatus recited in claim 3, wherein the lid includes a top wall and a lid sidewall extending downwardly from the top wall, the lid sidewall having a lower rim disposed opposite the top wall, and wherein the first handle is disposed on the lid sidewall adjacent the lower rim.

7. The apparatus recited in claim 6, wherein the first handle has a lower surface that is coplanar with the lower rim of the lid.

8. The apparatus recited in claim 3, wherein the at least one first handle includes a pair of first handles and the at least one second handle includes a pair of second handles, each of the pair of first handles extending from opposite sides of the lid, and each of the pair of second handles extending from opposite sides of the base.

9. An apparatus comprising:
   a culture dish including a base and a lid adapted to be disposed on the base, the base including a bottom wall, a rim and a sidewall extending upwardly from the bottom wall to the rim;
   at least one first handle extending from a sidewall of the lid; and
   at least one second handle extending from a portion of the sidewall of the base between the bottom wall and the rim, wherein the first handle overlies the second handle, the first handle having a first outer edge disposed opposite the sidewall of the lid and the second handle having a second outer edge disposed opposite the sidewall of the base, the first and second handles being arranged so that the first outer edge protrudes beyond the second outer edge when the lid is disposed on the base.

10. An apparatus comprising:
    a culture dish including a base and a lid adapted to be disposed on the base;
    at least one first handle extending from a sidewall of the lid; and
    at least one second handle extending from a sidewall of the base, wherein the first handle overlies the second handle, the first handle having a first outer edge disposed opposite the sidewall of the lid and the second handle having a second outer edge disposed opposite the sidewall of the base, the first and second handles being arranged so that the first outer edge protrudes beyond the second outer edge when the lid is disposed on the base, wherein each of the base and the lid includes at least two corners, the first handle being centered between the at least two corners of the lid and the second handle being centered between the at least two corners of the base.

11. An apparatus comprising:
    a culture dish including a base and a lid adapted to be disposed on the base;
    at least one first handle extending from a sidewall of the lid; and
    at least one second handle extending from a sidewall of the base, wherein the first handle overlies the second handle, the first handle having a first outer edge disposed opposite the sidewall of the lid and the second handle having a second outer edge disposed opposite the sidewall of the base, the first and second handles being arranged so that the first outer edge protrudes beyond the second outer edge when the lid is disposed on the base, wherein the lid includes a top wall and a lid sidewall extending downwardly from the top wall, the lid sidewall having a lower rim disposed opposite the top wall, and wherein the first handle is disposed on the lid sidewall adjacent the lower rim.

12. The apparatus recited in claim 11, wherein the first handle has a lower surface that is coplanar with the lower rim of the lid.

13. An apparatus comprising:
    a culture dish including a base and a lid adapted to be disposed on the base;
    at least one first handle extending from a sidewall of the lid; and
    at least one second handle extending from a sidewall of the base, wherein the first handle overlies the second handle, the first handle having a first outer edge disposed opposite the sidewall of the lid and the second handle having a second outer edge disposed opposite the sidewall of the base, the first and second handles being arranged so that the first outer edge protrudes beyond the second outer edge when the lid is disposed on the base, wherein the at least one first handle includes a pair of first handles and the at least one second handle includes a pair of second handles, each of the pair of first handles extending from opposite sides of the lid, and each of the pair of second handles extending from opposite sides of the base.

14. An apparatus comprising:

a culture dish including a base having a bottom wall, a rim and a sidewall extending upwardly from the bottom wall to the rim, the sidewall including a lower sidewall and an upper sidewall, the lower sidewall being disposed between the bottom wall and the upper sidewall, the upper sidewall being disposed between the lower sidewall and the rim, the lower sidewall being angled at a first angle relative to a vertical plane passing through the bottom wall, the upper sidewall being angled at a second angle relative to the vertical plane, the first angle being different than the second angle.

15. The apparatus recited in claim 14, wherein the lower sidewall and the upper sidewall intersect at a parting line, the lower sidewall extending upwardly from the bottom wall to the parting line, the upper sidewall extending upwardly from the parting line to the rim, the lower sidewall extending upwardly away from a vertical plane passing through the bottom wall, the upper sidewall extending upwardly toward the vertical plane.

16. The apparatus recited in claim 15, further comprising a lid adapted to cover the base, the lid including a top wall, a lower rim and a lid sidewall extending downwardly from the top wall to the lower rim, the lid sidewall extending downwardly away from the vertical plane at the second angle.

17. The apparatus recited in claim 14, further comprising a lid adapted to cover the base, the lid including a top wall, a lower rim and a lid sidewall extending downwardly from the top wall to the lower rim, the lid sidewall extending downwardly away from the vertical plane at the second angle.

18. An apparatus comprising:

a culture dish including a base having a bottom-wall, a rim and a sidewall extending upwardly from the bottom wall to the rim, the lower sidewall and the upper sidewall intersecting at a parting line, the lower sidewall extending upwardly from the bottom wall to the parting line, the upper sidewall extending upwardly from the parting line to the rim, the lower sidewall extending upwardly away from a vertical plane passing through the bottom wall, the upper sidewall extending upwardly toward the vertical plane.

19. The apparatus recited in claim 18, further comprising at least one handle extending from the sidewall.

20. The apparatus recited in claim 19, wherein the at least one handle is disposed on the lower sidewall.

21. The apparatus recited in claim 20, wherein the at least one handle extends from the lower sidewall at the parting line.

22. The apparatus recited in claim 18, further comprising a lid adapted to cover the base, the lid including a top wall, a lower rim and a lid sidewall extending downwardly from the top wall to the lower rim, the lid sidewall extending downwardly away from the vertical plane.

* * * * *